(12) United States Patent
Alsheddi et al.

(10) Patent No.: US 8,014,955 B2
(45) Date of Patent: Sep. 6, 2011

(54) METHOD OF IDENTIFYING UNIQUE TARGET SEQUENCE

(75) Inventors: Tariq Alsheddi, Vienna, VA (US); Anna Baranova, Fairfax, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 1143 days.

(21) Appl. No.: 11/475,261

(22) Filed: Jun. 27, 2006

(65) Prior Publication Data

US 2007/0161012 A1 Jul. 12, 2007

Related U.S. Application Data

(60) Provisional application No. 60/693,781, filed on Jun. 27, 2005.

(51) Int. Cl.
  *G01N 33/48* (2006.01)
  *C12Q 1/68* (2006.01)
  *C07H 21/04* (2006.01)

(52) U.S. Cl. ............ 702/19; 436/6; 536/23.1; 536/24.1; 702/20

(58) Field of Classification Search ................ None
See application file for complete search history.

*Primary Examiner* — Shubo Zhou
(74) *Attorney, Agent, or Firm* — Brendan O. Baggot

(57) ABSTRACT

Described are methods and systems for designing target-specific oligonucleotides of L-length. The method comprises a) parsing a polynucleotide target into overlapping sequences of N-length nucleotides, creating a kernel set; b) performing step a) reiteratively for each target until each it is associated with its own kernel set; c) removing N-length kernels from the kernel sets which are redundant; d) concatenating X-length nucleotide suffixes to each N-length nucleotide kernel to create L-length oligonucleotide sets; e) ordering L-length nucleotides within each set of step d) by their nucleotide position within the target; f) retaining or rejecting an L-length oligonucleotide, based on the presence or absence of each of the X consecutive and overlapping N-length kernels; and g) performing step f) reiteratively. Step g) can be modified to parse L-length oligonucleotide sequences into overlapping Y-length nucleotides to create a set of Y-length kernels; and h) removing certain kernels that meet specified conditions.

8 Claims, 1 Drawing Sheet

METHOD OF IDENTIFYING UNIQUE TARGET SEQUENCE

This application claims the benefit of U.S. provisional patent application Ser. No. 60/693,781 filed Jun. 27, 2005, the entire disclosure of which is hereby incorporated by reference.

BACKGROUND OF THE INVENTION

Currently, there are three widely used general algorithms that are available for nucleotide and amino acid sequence similarity searching. These include Smith-Waterman, FASTA and BLAST. The latter is a simplification of the Smith-Waterman algorithm which is also known as the maximal segment pairs algorithm. The first step in FASTA and BLAST is a "word" search with a specific word size (usually two for proteins and six for nucleic acids). For each such "word" in both sequences, BLAST will compare them and assign that punctual match a score. BLAST allows for mismatches and ambiguity in comparisons. BLAST then tries to join words and find the maximal segment of contiguous matching words. This is called a maximal segment pair (MSP) and represents a matching region containing no gaps. The scores of each word are added and a global score for the MSP is computed. BLAST deals with each of these regions separately, i.e., BLAST does not allow gaps inside matches. As it finds matches, BLAST makes decisions on how to align them based on a statistical analysis of the sequences, discarding what it determines to be possibly a random or meaningless match. This speeds the analysis up, but has a detrimental consequence: matches of short or frequently appearing sequences may be lost, leading to potential off-target annealing sites within a selected oligonucleotide sequence.

FASTA works on a different set of assumptions than BLAST, and hence provides different results. FASTA speeds things up by comparing several residues at once. It looks for exact matches of this small number of residues (word) and does not consider ambiguity or approximate matches in the comparison. Once all word matches have been found, FASTA also tries to join them into regions. At the next stage FASTA takes the 10 best matching regions for each analyzed oligonucleotide and tries to join them into a bigger one even although they might be separated: FASTA selects the similarity region accommodating gaps, and computes an overall score for the match with the gaps. Finally, FASTA sorts sequences by the best similarity region (after joining matches with gaps) found and generates a better quality alignment using the Smith-Waterman algorithm to calculate a new and more accurate score. If this score exceeds a given threshold depending on its length, the sequence is considered an acceptable match. This means that just like BLAST, FASTA may reject some possibly biologically significant matches with low statistical scores. This may result in the loss of some significant matches in low complexity or very short sequences/matches/motifs. Both BLAST and FASTA are more reliable when working with relatively large polynucleotides, and less adequate while working on short polynucleotides.

The Smith-Waterman (SW) algorithm is more sensitive than either BLAST or FASTA. This is because BLAST and FASTA place additional restrictions on the alignments that they report in order to speed up their operation, but the Smith-Waterman places no restriction on the alignment it reports other than that it have a positive score in terms of the similarity table used to score the alignment. This makes the Smith-Waterman much more rigorous, but also more sensitive. Since SW searching is exhaustive, it is the slowest method. We offer an alternative to Smith-Waterman (SW) algorithm, that allow exhaustive cataloguing of the perfect matches of the meaningful length in any set of sequences of interest (e.g. human transcriptome).

DESCRIPTION OF THE INVENTION

Figure 1:
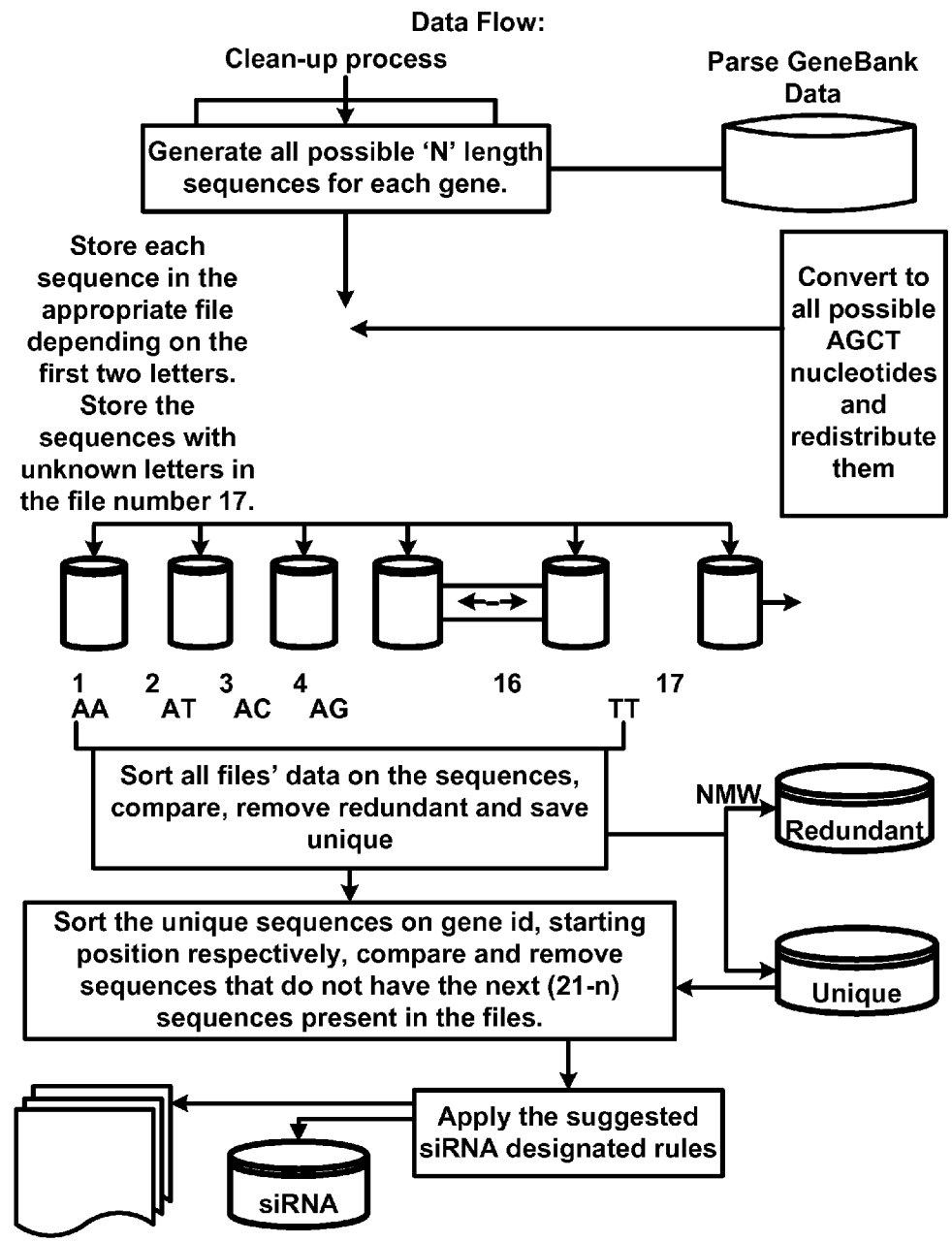
FIG. 1 shows a flow diagram of a method of a method for designing unique polynucleotide targets.

The present invention provides methods and systems for identifying unique polynucleotide sequences within a larger polynucleotide sequence. The methods and systems are useful for designing unique polynucleotides for any purpose, e.g., as probes, primers, transcription or translation modulators, siRNAs, capture labels, ribozymes, etc. The polynucleotides can be used in silencing or interference RNA ("siRNA") technologies, polymerase chain reaction ("PCR"), including quantitative PCR, microarrays, and any hybridization strategy that utilizes oligonucleotides to detect or label nucleic acids. The methods can be used to validate and assess the specificity and off-target annealing of target-specific polynucleotides (e.g., siRNAs) that have been generated by other methods.

The present invention utilizes a "divide and conquer" approach to identifying specific polynucleotide probes. The major source of off-target annealing and imperfect specificity of M-length oligonucleotides is a partial homology to off-target sequences of length N, where M>N, and N is contained inside of M. For example, an oligonucleotide consisting of the sequence AGCgatcgtacgatgctagggTA (SEQ ID NO: 1) (M=23) which is specific to gene X, will anneal off-target to the complement of CGGgatcgtacgatgctaggCTT (SEQ ID NO: 2) which is specific to gene Y because they share identical internal kernel sequences, i.e., "gatcgtacgatgctagg" (SEQ ID NO: 3), where N=17.

The present invention provides systems and methods for designing or identifying a target-specific oligonucleotide sequence having an L-length of a polynucleotide population comprising polynucleotide targets, comprising one or more of the following steps in any effective order, e.g., a) exhaustively parsing a polynucleotide target into overlapping polynucleotide sequences of N-length nucleotides to create an N-length nucleotide kernel set for each target;

b) performing step a) reiteratively for each polynucleotide target that is a member of the polynucleotide population, until each polynucleotide target is associated with its own N-length nucleotide kernel set;

c) removing N-length nucleotide kernels from N-length nucleotide kernel sets which are present in more than one N-length nucleotide kernel set;

d) concatenating X-length nucleotide suffixes to each N-length nucleotide kernel to create L-length (N+X) oligonucleotide sequences sets for each polynucleotide target, where the suffix consists of an X-length sequence of nucleotides directly adjacent and contiguous with the 3' end or 5' end of the N-length nucleotide kernel;

e) ordering L-length nucleotides consecutively within each set of step d) by their nucleotide position within the target polynucleotide;

f) 1) retaining an L-length oligonucleotide, when each of the X consecutive and overlapping N-length kernels are present after step e), where each of the X consecutive kernels comprise at least one nucleotide of the X-length suffix; and f) 2) rejecting an L-length oligonucleotide, when at least one of the X consecutive and overlapping N-length kernels is absent after steps e), where each of the X consecutive kernels comprise at least one nucleotide of the X-length suffix; and g) performing step f) reiteratively, beginning with the X+1 N-length kernel when all X-length kernels are present; or beginning with the kernel immediately following the absent kernel.

Step g) can be substituted by the following steps:

g) exhaustively parsing L-length oligonucleotide sequences of step f) into overlapping polynucleotide sequences of Y-length nucleotides to create a complete set of Y-length nucleotide kernels for each polynucleotide target, wherein each Y-length kernel comprises at least one nucleotide of the X-length nucleotide suffix; and h) removing Y-length nucleotide kernels from Y-length nucleotide kernel sets that meet at least one specified condition, e.g., where the condition is that any kernel which is repeated more than once in more than one kernel set is eliminated.

Step d) can be more broadly carried by: d') choosing X-length nucleotide suffixes for each N-length nucleotide kernel, wherein the suffix consists of an X-length sequence of nucleotides that is upstream or downstream of the kernel, and separated by a gap of nucleotides. When d') is performed, the steps g) and h) can be carried out with respect to the suffix sequence or with respect to the nucleotide sequence within the gap. Furthermore, the gap sequence can be analyzed for the presence or absence of one or more characteristics or specified conditions.

In a first step of the present invention, "kernel" sequences of N-length are selected for each polynucleotide target sequence. The targets are "exhaustively parsed" indicating that the target is divided into every possible N-length fragment, e.g., by scanning across the target sequence one nucleotide at a time. This step is performed for each target in the polynucleotide population. At the finish, each target is associated with a set of N-length kernels.

A computer algorithm can be routinely created which automatically extracts ("parsing") sequences by sequentially sliding a window of N-length nucleotides, at least one nucleotide at a time, across any given sequence of interest. The size of the window can be varied, depending upon the complexity and size of the polynucleotide collection, as well as the purpose of the target-specific nucleotide. For example, N can be 10, 11, 12, 13, 14, 15, 16, 17, 18, 20, 22, etc., nucleotides in length.

To eliminate sources of non-specific annealing where an oligonucleotide is capable of binding to more than one target, N-length kernels are rejected which are present in more than one kernel set. In addition to redundancy, other conditions can be applied for rejecting N-length nucleotide kernels, e.g., having a specified nucleotide content (such as GC content), having a specified melting temperature, having a specified secondary structure, etc.

Kernels are retained or rejected on the following basis:

If a kernel with N-length appears in gene A, 0 times; in gene B, 0 times; in gene C, 0 times; and, in gene D, 4 times, this kernel is considered unique to the target, and is retained in the set;

if kernel with N-length appears in gene A, 0 times; in gene B, 1 times; in gene C, 0 times; in gene D, 0 times, this kernel is considered unique and is retained in the set;

if kernel with N-length appears in gene A, 0 times; in gene B, 1 times; in gene C, 0 times; in gene D, 1 times, this kernel is not considered unique and is excluded or rejected from the set.

Suffix sequences of X-length (a contiguous stretch of polynucleotides) are chosen which are either upstream or downstream (5' or 3') of the N-length kernel. The suffix sequence can be directly adjacent and contiguous with a kernel, but it can also be separated by a gap of one or more nucleotides depending on the final purpose of the oligonucleotide. For example, gaps maybe introduced when hairpin or other secondary structures are to be present in the oligonucleotide.

X can be of any desired length, once again depending on, e.g., the polynucleotide complexity and/or size, and the purpose for which the final oligonucleotide is to be used. Examples of sizes include, e.g., of 4, 6, 8, 10, 11, 12, 13, 15, etc., nucleotides in length.

The suffixes are concatenated to the kernel to create a polynucleotide of the desired L-length (i.e., N+X). The resulting L-length oligonucleotides can be ordered consecutively by their nucleotide position within the target polynucleotide. For example, if the parsing step started at position 1 of the target sequence, and certain kernels were removed because of their redundancy in other kernel sets, consecutive ordering of the remaining kernels could result in kernels starting at the following nucleotide positions: 1, 2, 4, 5, 6, 7, 8, 10, . . . etc., where kernels 3 and 9 were removed because they were present in other kernel sets.

The ordering step provides a time-saving and efficient approach for eliminating L-length oligonucleotides which comprise sequences that have the potential to anneal off-target (i.e., to a different target polynucleotide in the population). This is determined by looking at X consecutive N-length kernels within each L-length oligonucleotide sequence, where each kernel contains at least one nucleotide of the suffix, and rejecting those in which there is a gap in the consecutive numbering. The presence of a gap indicates the presence of a redundant kernel (i.e., a kernel that appears in least one other target sequence), and therefore a source of off-target annealing.

A target-specific oligonucleotide sequence can be identified from any database, population, or collection of polynucleotide sequences without limitation. These include genomic sequences, transcriptomes, cDNA libraries, collections of expressed sequences (e.g., from viruses, bacteria, fungi, animals, mammals, plants, etc.), genomic sequences (e.g., from viruses, bacteria, fungi, animals, mammals, plants, etc.), etc. The terms "database", "collection," or "population" indicate the set of sequences that are analyzed for the presence of target specific sequences.

The polynucleotide population can represent a single species or type of organism, or it can contain multiple species or types. For example, a goal can be to design an siRNA that is specific to a bacteria, virus (such as HIV, Hepatitis C, Ebola, influenza, etc.), or other pathogen, and which does not occur in the pathogen host. For this task, nucleotide sequences from the pathogen can be included in the population of host sequences in order to design an siRNA that will anneal to the pathogen nucleic acid, but not to the host's.

The phrase "specific oligonucleotide," "target-specific," and the like, have a functional meaning that the oligonucleotide can be used to identify, detect the presence or absence of, mutagenize, or to otherwise manipulate a target gene in a sample, and distinguish it from non-target genes. The oligonucleotide is specific in the sense that it binds to its target above background noise ("non-specific binding"). A specific sequence is a defined order of nucleotides which occurs in the polynucleotide, and which is characteristic of that target sequence, and substantially no non-target sequences.

Any suitable computer algorithm can be used to implement the steps described above. There is no restriction as to the computer language or how the implementation is achieved. Useful computer languages include, e.g., C++, Java, Perl, Python, and Fortran.

The present invention also provides computer systems comprising a computer readable medium having one or more software components encoded thereon in computer readable form, wherein the one or more software components may be loaded into a memory of a computer system and cause a processor interconnected with said memory to execute steps of a method in accordance with the present invention.

All references, publications, patents, and patent applications mentioned herein are hereby incorporated by reference in their entirety.

EXAMPLES

We have developed a new algorithm that allows one to map all unique short-string sequences further we called "the target" with lengths (N)=9, 10, . . . , 15 nt in size within large sets of sequences, e.g. a set of all known Mouse genes. The algorithm assures the uniqueness of the "target" in the non-redundant set of the murine mRNAs. The "target" will be considered unique if no other gene contains an identical short-string sequence to it; otherwise all the identical short-string sequences including primary target will be rejected. The candidate antisense strand of siRNA is formed by concatenating the unique target with its suffix of length equal to (21−N). All candidate siRNA antisense sequences are referred to by sense strand, starting at position 1 at 5' end, which corresponds to position 21 of the antisense strand. Our efficient software avoids off-target gene silencing to numerate potential cross-hybridization candidates that the widely used BLAST search may overlook. Our Algorithm can be used to search the entire sequence database to check whether individual siRNA oligonucleotides potentially cross-hybridize with irrelevant sequences.

Materials and Methods

Computational Methods:

The scripts for parsing the GENBANK files, generating the 'N' length sequences, distributing them on the files, the redundant remover script and the proteomic level redundant remover scripts are written in the Perl programming language. The MS Access datanucleotide is used for the sorting process. The applet for interactive selection of siRNA antisense from the datanucleotide is programmed in Java.

The comprehensive search throughout the mouse transcriptome:

As a test set for siRNA prediction we used 18862 full-size murine mRNAs described in the GENBANK database. We retrieved all murine Unigene clusters containing mRNA sequences. To ensure that this set of mRNA is non-redundant we selected only one mRNA out of each cluster, preference was given to Curated Nucleotide Sequence mRNA Records identified by Ac.Nums abbreviations that start with NM. In case of absence of any NM-mRNA record mRNA longest mRNA was retrieved. In case of the presence of two or more NM-mRNAs usually representing alternatively spliced mRNA isoforms longest NM-mRNA was retrieved. Retrieved non-redundant mRNAs were concatenated in the text file with preserved mRNA identificators. Nucleotides shown in lowercase were removed from NM sequences as they represent less reliable sequences or repeats.

The algorithm tests the uniqueness of a sequence of length 'N' in the non-redundant set of the murine mRNAs. The sequence of length 'N', further called "the target", will be considered unique, if no other genes contain an identical target; otherwise all the identical targets including primary target will be rejected. The candidate antisense strand of siRNA is formed by concatenating the unique target with the target suffix of length equal to (21−N). All candidate siRNA antisense sequences are referred to by sense strand, starting at position 1 at 5' end, which corresponds to position 21 of the antisense strand.

The Algorithm:

The main purpose of this algorithm is to generate 21 bp siRNA sequences that are characterized by minimal off-target hybridization. The algorithm steps are as follow:

1—Generate all possible sequences with length 'N': A model mouse transcriptome was transformed into set of sequence fragments of length "N" where first nucleotide of the first fragment corresponds to Position 1 in Gene 1, first nucleotide of the second fragment corresponds to Position 2 in Gene 1 etc. Generated sequences stored in master files according to their first dinucleotide. Sequences that contain nucleotides other than ACGT was stored in different file.

2—Removal of the redundant targets: we sorted the records in the master-files ascending on the target sequence field. All duplicated targets were removed from the dataset.

3—Check for the occurrence of the target in the candidate siRNA antisense: Unique targets from the previous step will concatenate to their suffix. This 21 base pair in length sequence could contain a chimeric target identical to one or more targets from another gene which has been removed in the previous step.

To avoid generation of chimera, we check for the presence of the (21−N) targets downstream the target under study, which represent all possible fragments in the 21 base pair sequence which have starting points (P)=(P+1, P+2, P+21−N) and each of length=N. In order to do this checking, we sorted all unique targets according to their Gene IDs, P of the target, respectively (see. FIG. 1); then we check for the absence of any of the (21−N) adjacent targets downstream the target under study. The absence of any target means that it is identical to another target and both of them excluded from the data set in the previous step. If they are all present (the 21−N targets downstream) this mean the target under study is unique.

| Gene Id. | Target | Suffix | P |
|---|---|---|---|
| gi = 31560634 | AGTACAGCTTGTTG | CGCTCTG | 73 (SEQ ID NO: 4) |
| gi = 31560634 | GTACAGCTTGTTGC | GCTCTGA | 74 (SEQ ID NO: 5) |
| gi = 31560634 | TACAGCTTGTTGCG | CTCTGAA | 75 (SEQ ID NO: 6) |
| gi = 31560634 | ACAGCTTGTTGCGC | TCTGAAT | 76 (SEQ ID NO: 7) |
| gi = 31560634 | CAGCTTGTTGCGCT | CTGAATA | 77 SEQ ID NO: 8) |
| gi = 31560634 | AGCTTGTTGCGCTC | TGAATAT | 78 (SEQ ID NO: 9) |
| gi = 31560634 | GCTTGTTGCGCTCT | GAATATA | 79 (SEQ ID NO: 10) |
| gi = 31560634 | CTTGTTGCGCTCTG | AATATAT | 80 (SEQ ID NO: 11) |

-continued

| Gene Id. | Target | Suffix | P |
|---|---|---|---|
| gi = 31560634 | TTGTTGCGCTCTGA | ATATATT | 81 |
| | | (SEQ ID NO: 12) | |

4—Apply the suggested siRNA designing rules: The resulted dataset has siRNA antisense sequences where no other gene has an identical fragment with length 'N' to any part of it. Any suggested rules for siRNA designing could be applied to maximize the efficiency.

FIG. 1: It is known from the previous step that all targets (N=14) in this dataset are unique. Now, For the target 'AGTACAGCTTGTTG' (SEQ ID NO: 13), which start at position P=73, It is clear that fragment starting from the second base "G", with N=14, and ending at "C" (the first base in its suffix) could be identical to another target from another gene, in such case it supposed to be removed from the previous step and will not show up in this dataset. (Note that this fragment is represented as next target with P=74) So if all (21−N) targets downstream of the target under study are present, then this 21 by siRNA contains no fragment of length N that identical to any part of another gene.

Results:

We ran the algorithm with target length N=9, 10, 11, 12, 13, 14 and 15 on mouse. A brief summary of the results is shown in the following table:

| N (Length of the Target) | # of siRNA | % of the proteomics |
|---|---|---|
| 9 | 0 | 0 |
| 10 | 0 | 0 |
| 11 | 5 | 0.03% |
| 12 | 15,837 | 28% |
| 13 | 88,746 | 97% |
| 14 | 8,161,000 | 99.7% |
| 15 | 22,950,857 | 100% |

The preceding examples can be repeated with similar success by substituting the generically or specifically described conditions of this invention for those used in the preceding examples.

From the foregoing description, one skilled in the art can easily ascertain the essential characteristics of this invention and, without departing from the spirit and scope thereof, can make various changes and modifications of the invention, to adapt it to various usages and conditions.

What we claimed:

1. A non-transient tangible computer readable medium containing computer readable instructions that when executed by one or more processors, cause the one or more processors to execute a method for designing a target-specific oligonucleotide sequence having an L-length in a polynucleotide population comprising polynucleotide targets, the method comprising:
   a) exhaustively parsing a polynucleotide target into overlapping polynucleotide sequences of N-length nucleotides to create an N-length nucleotides kernel set for each target;
   b) performing step a) reiteratively for each polynucleotide target that is a member of the polynucleotide population, until each polynucleotide target is associated with its own N-length nucleotide kernel set;
   c) removing N-length nucleotide kernels from the N-length nucleotide kernel sets which are present in more than one N-length nucleotide kernel set;
   d) choosing X-length nucleotide suffixes for each N-length nucleotide kernel, wherein the suffix consists of an X-length sequence of nucleotides that is upstream or downstream of the kernel, and optionally separated by a gap of nucleotides;
   e) ordering L-length nucleotides consecutively within each set of step d) by their nucleotide position within the target polynucleotide, wherein each L-length nucleotide comprises consecutive and overlapping kernels;
   f) 1) retaining an L-length oligonucleotide, if each of the X consecutive and overlapping N-length kernels are present after step e), wherein each of the X consecutive kernels comprise at least one nucleotide of the X-length suffix; and
   f) 2) rejecting an L-length oligonucleotide, if at least one of the X consecutive and overlapping N-length kernels is absent after steps e), wherein each of the X consecutive kernels comprise at least one nucleotide of the X-length suffix;
   g) performing steps f)1 and f)2 reiteratively, beginning with the X+1 N-length kernel when all X-length suffixes are present; or beginning with the kernel immediately following the absent suffix; and
   h) displaying the results of step (g) in a computer readable format to determine the identity of said target specific oligonucleotide sequence.

2. The non-transient tangible computer readable medium A according to claim 1, wherein step d) is performed by concatenating X-length nucleotide suffixes to each N-length nucleotide kernel to create L-length (N+X) oligonucleotide sequences sets for each polynucleotide target, where the suffix consists of an X-length sequence of nucleotides directly adjacent and contiguous with the 3' end or 5' end of the N-length nucleotide kernel.

3. The non-transient tangible computer readable medium according to claim 1, wherein N is 10-22.

4. The non-transient tangible computer readable medium according to claim 1, wherein X is 4-15.

5. A computer system comprising a non-transient tangible computer readable medium containing computer readable instructions for performing the method according to claim 1.

6. A non-transient tangible computer readable medium containing computer readable instructions that when executed by one or more processors, cause the one or more processors to execute a method for designing a target-specific oligonucleotide sequence having an L-length in a polynucleotide population comprising polynucleotide targets, comprising:
   a) exhaustively parsing a polynucleotide target into overlapping polynucleotide sequences of N-length nucleotides to create an N-length nucleotide kernel set for each target;
   b) performing step a) reiteratively for each polynucleotide target that is a member of the polynucleotide population, until each polynucleotide target is associated with its own N-length nucleotide kernel set;
   c) removing N-length nucleotide kernels from the N-length nucleotide kernel sets which are present in more than one N-length nucleotide kernel set;
   d) choosing X-length nucleotide suffixes for each N-length nucleotide kernel, wherein the suffix consists of an X-length sequence of nucleotides that is upstream or downstream of the kernel, and optionally separated by a gap of nucleotides;
   e) ordering L-length nucleotides consecutively within each set of step d) by their nucleotide position within the target polynucleotide, wherein each L-length nucleotide comprises consecutive and overlapping kernels;
   f) 1) retaining an L-length oligonucleotide if each of the X consecutive and overlapping N-length kernels are present after step e), wherein each of the X consecutive kernels comprise at least one nucleotide of the X-length suffix; and
   f) 2) rejecting an L-length oligonucleotide if at least one of the X consecutive and overlapping N-length kernels is absent after steps e), wherein each of the X consecutive kernels comprise at least one nucleotide of the X-length suffix;
   g) exhaustively parsing L-length oligonucleotide sequences of step f) 1) into overlapping polynucleotide sequences of Y-length nucleotides to create a complete set of Y-length nucleotide kernels for each polynucleotide target, wherein each Y-length kernel comprises at least one nucleotide of the X-length nucleotide suffix; and
   h) removing Y-length nucleotide kernels from Y-length nucleotide kernel sets that meet at least one specified condition; and
   i) displaying the results of step (h) in a computer readable format to determine the identity of said target specific oligonucleotide sequence.

7. The non-transient tangible computer readable medium according to claim 6, wherein step d) is performed by concatenating X-length nucleotide suffixes to each N-length nucleotide kernel to create L-length (N+X) oligonucleotide sequences set for each polynucleotide target, where the suffix consists of an X-length sequence of nucleotides directly adjacent contiguous with the 3' and or 5' end of the N-length nucleotide kernel.

8. The non-transient tangible computer readable medium according to claim 6, wherein the condition in step h) is that any kernel which is repeated more than once in more than one kernel set is eliminated.

* * * * *

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agcgatcgta cgatgctagg gta                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgggatcgta cgatgctagg ctt                                              23

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatcgtacga tgctagg                                                     17

<210> SEQ ID NO 4
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 4
agtacagctt gttgcgctct g                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtacagcttg ttgcgctctg a                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tacagcttgt tgcgctctga a                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
acagcttgtt gcgctctgaa t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cagcttgttg cgctctgaat a                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agcttgttgc gctctgaata t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                                                                    oligonucleotide

<400> SEQUENCE: 10
gcttgttgcg ctctgaatat a                                                          21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cttgttgcgc tctgaatata t                                                          21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttgttgcgct ctgaatatat t                                                          21

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agtacagctt gttg                                                                  14
```